(12) United States Patent
Brusilovski et al.

(10) Patent No.: US 11,083,615 B1
(45) Date of Patent: Aug. 10, 2021

(54) DEVICE FOR WALKING WITH A KNEE JOINT AFFECTED ON BOTH SIDES OF THE JOINT

(71) Applicants: Zinovi Brusilovski, Kiryat-Gat (IL); Refael Bronstein, Kefar Sava (IL); Anna Rubin-Brusilovski, San Diego, CA (US)

(72) Inventors: Zinovi Brusilovski, Kiryat-Gat (IL); Refael Bronstein, Kefar Sava (IL); Anna Rubin-Brusilovski, San Diego, CA (US)

( * ) Notice: Subject to any disclaimer, the term of this patent is extended or adjusted under 35 U.S.C. 154(b) by 0 days.

(21) Appl. No.: 17/072,829

(22) Filed: Oct. 16, 2020

(51) Int. Cl.
*A61F 5/01* (2006.01)
*B25J 9/10* (2006.01)
*B25J 9/00* (2006.01)

(52) U.S. Cl.
CPC .......... *A61F 5/0123* (2013.01); *B25J 9/0006* (2013.01); *B25J 9/10* (2013.01); *A61F 2005/0137* (2013.01)

(58) Field of Classification Search
CPC ........ A61F 5/0123; A61F 5/0102; A61F 5/01; A61F 5/00; A61F 5/0113; A61F 5/0127; A61F 5/0111; A61F 5/0118; A61F 5/0125; A61F 5/013; A61F 2/30; A61F 2005/0139; A61F 2005/0137; A61F 2005/0181; A61F 2005/0174; A61F 2005/0134; A61F 2005/0146; A61F 2005/0155; A61F 2005/0167; A61F 2005/0169; A61F 2005/0179; B25J 9/0006; B25J 9/10; B25J 9/0137; A61N 2/06; A44C 25/00; A63B 21/00192; A63B 21/005; A63B 21/0051; A61H 2201/12; A61H 2201/1207; A61H 2201/1246; A61H 2201/164; A61H 2201/1642; A61H 1/0237; A61H 1/024; A61H 1/0244; A61H 3/00
USPC ........ 602/16; 623/13, 18, 20, 21, 22, 23, 24, 623/27, 33, 34, 35, 36, 37, 38, 39, 18.12
See application file for complete search history.

(56) References Cited

U.S. PATENT DOCUMENTS

| | | | |
|---|---|---|---|
| 5,018,514 A | 5/1991 | Grood et al. | |
| 5,152,302 A | 10/1992 | Fareed | |
| 5,879,386 A | 3/1999 | Jore | |
| 8,057,550 B2 | 11/2011 | Clausen et al. | |
| 8,679,046 B2* | 3/2014 | Ital | A61F 5/0125 602/23 |
| 9,416,838 B2 | 8/2016 | Garrish | |
| 2003/0109817 A1* | 6/2003 | Berl | A61F 5/0123 602/5 |
| 2003/0187510 A1* | 10/2003 | Hyde | A61F 2/3868 623/18.12 |
| 2010/0056846 A1* | 3/2010 | Friberg | A63B 21/4025 600/9 |

(Continued)

*Primary Examiner* — Alireza Nia
*Assistant Examiner* — Daniel A Miller
(74) *Attorney, Agent, or Firm* — Katterle Nupp LLC; Paul Katterle; Robert Nupp

(57) ABSTRACT

Disclosed is a method and device for reducing a load on a knee joint in the course of walking. The device reduces the load on both compartments of a damaged knee. The device includes a plurality of permanent magnets configured to maintain a consistent resistance to a load on a leg of a person. The device reduces the load exerted by the femur on the tibia and keeps the load reduced during the walking, alleviating a pain caused by the worn-out cartilage and the bone-on-bone phenomenon.

12 Claims, 15 Drawing Sheets

(56) References Cited

U.S. PATENT DOCUMENTS

| | | |
|---|---|---|
| 2012/0150086 A1 | 6/2012 | Cohen |
| 2014/0100410 A1* | 4/2014 | Balzer ................... A61N 2/06 600/9 |
| 2014/0163306 A1 | 6/2014 | Sykes |
| 2015/0265429 A1 | 9/2015 | Jonsson et al. |
| 2019/0183715 A1 | 6/2019 | Kapure et al. |
| 2019/0216627 A1 | 7/2019 | Requa |
| 2019/0274859 A1 | 9/2019 | Boucher et al. |
| 2019/0290464 A1 | 9/2019 | Fleming |
| 2019/0298563 A1 | 10/2019 | Heiberg |
| 2019/0308028 A1 | 10/2019 | White |
| 2019/0350735 A1 | 11/2019 | Ingimundarson et al. |

\* cited by examiner

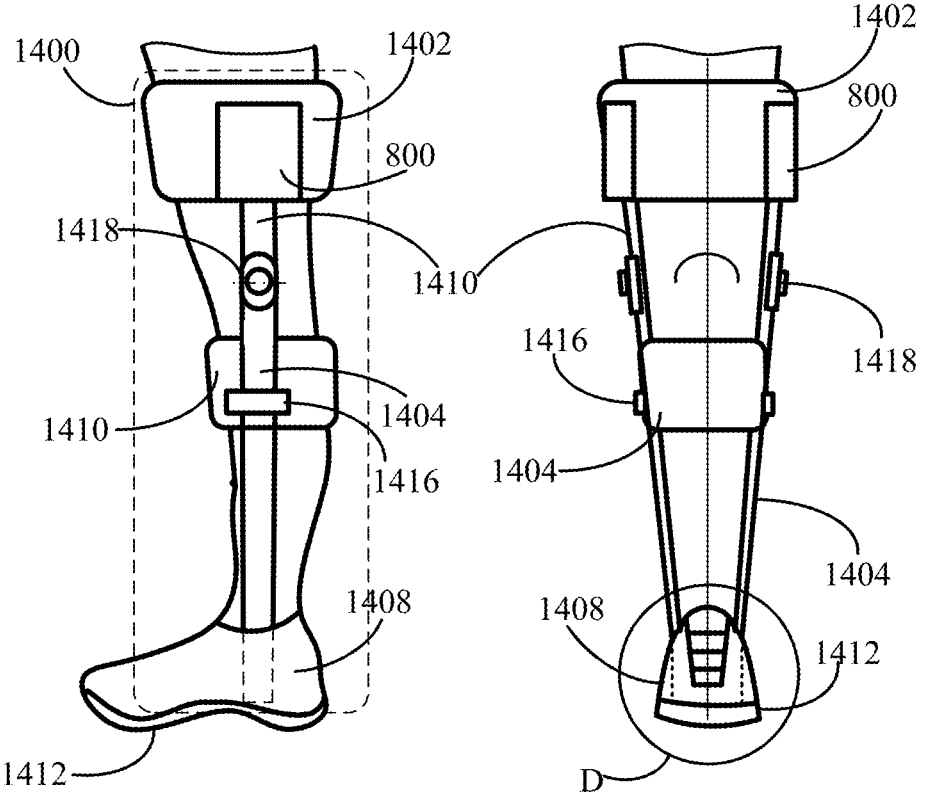
FIG. 14    FIG. 15
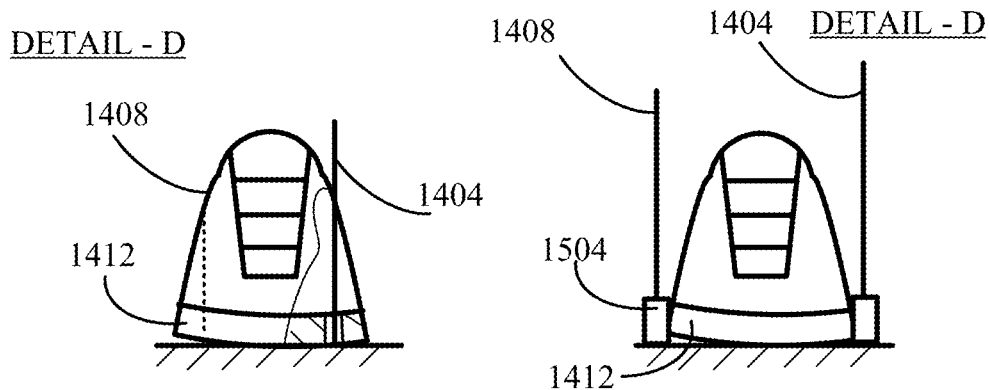
DETAIL - D    DETAIL - D

VARIOUS VERSIONS OF DETAIL - F

DEVICE FOR WALKING WITH A KNEE JOINT AFFECTED ON BOTH SIDES OF THE JOINT

TECHNICAL FIELD

The present disclosure relates to a device and method of using permanent magnets in braces to significantly reduce the pressure on both compartments of the affected knee joint.

BACKGROUND

The knee is one of the weakest joints in the human body. It is the articulating joint connecting the tibia and femur. In the course of almost every daily activity, different and significant loads act on the knee. These loads could cause different problems of the knee joint. Devices known as knee braces are supposed to alleviate some of the knee problems.

There are several types of knee braces. Each of the types of knee braces is used to alleviate different abnormal conditions of the knee. The braces do not cure abnormal conditions of the joints; they help to decrease stress and pain in a particular joint.

Some knee braces, for example, unloader braces, improve user mobility and reduce knee pain while at rest. Unloader knee braces are designed to transfer pressure inside the knee, "unloading" one side (damaged) of the joint to the other, not damaged side or compartment of the joint. In other words, the unloading knee brace does not exactly make what its name suggests—it transfers the load from the affected side of the joint to the healthier side of the joint.

Some knee braces, termed rehabilitation braces facilitate an injured or operated knee healing. Such braces are used, for example, in a knee post-operational period. There are braces that create an assisting force that helps the user bend and extend the legs. For example, US 2019/0060100, US 2018/0078399, and US 2015/0119777 all to Garrish use hydraulic devices for assisting the extension and/or flexing of a limb.

Some braces are designed for sports. Athletes often wear such braces after an injury has healed. They stabilize the knee and control movement to prevent re-injury. Some braces are designed to protect the knees from injury during contact sports, for example, football.

Most braces use mechanical springs that are configured to facilitate a specific function performed by the brace user, for example, when a person moves up the stairs.

Some devices are reducing joint pain use magnets. The magnets are inserted into the joint by surgery. US20050251080 to Hyde, U.S. Pat. No. 8,029,570 to Barnes, and U.S. Pat. No. 5,879,386 to Jore disclose such devices. Solutions described in the above three patents generate on the knee unwanted stretching effect when a person is sitting, in a recumbent position, and when the leg is moved in the air while walking.

SUMMARY

Disclosed is a method and device for reducing a load on a knee joint in the course of walking. The device reduces the load on both compartments of a damaged knee. The device includes a plurality of permanent magnets configured to maintain a consistent resistance to a load on a leg of a person. The device reduces the load exerted by the femur on the tibia and keeps the load reduced during the walking, alleviating a pain caused by the worn-out cartilage and the bone-on-bone phenomenon.

The principles of operation of the device will be explained on an example using three magnets, although any other number of uneven or even magnets could be used. The device configured to maintain a consistent resistance to displacement force includes the first substrate with three permanent magnets. One of the permanent magnets is located between a first marginal magnet and a third marginal magnet and adapted to repel one marginal magnet and attract another marginal magnet. The device further includes a second substrate located opposite the first substrate with a pair of permanent magnets adapted to repel each other. The assembly of the first substrate and a second substrate interspaces the pair of permanent magnets of the second substrate between the three permanent magnets of the first substrate. The assembly of the first substrate with three permanent magnets and the second substrate with a pair of permanent magnets have freedom of movement relative to each other. The first substrate and the second substrate are made of a material not affected by a magnetic field. The magnetic field of each of the magnets is 0.2-10.0 Tesla. In some examples, at least one of the permanent magnets is a magnet divided into two parts.

The device could be built-in into a joint brace, for example, a knee brace. The joint brace is adapted to be secured onto a body part on the side of a joint. In use, one of the substrates remains static, and the other substrate adapted to be secured onto a body part moves with the body part. The interaction forces between the permanent magnets oppose the forces caused by the weight of a person and reduce the pressure between the bones meeting at the knee. The forces developed by the permanent magnets reduce the load on both compartments of the knee and facilitate walking and sitting of a person wearing the joint brace.

In another example, the device for reducing a load on a knee joint during the walking includes a fixed ring to be worn on a sigh of a person and a movable ring. The rings are populated by a plurality of permanent magnets oriented to repel a plurality of magnets located on the other ring. One or more rigid levers connect the movable ring to a hinge located at a knee level. Another pair of levers with a proximal end connected to a hinge and a distal end resting on a floor pushes the movable ring towards the fixed ring. The repelling forces acting between the plurality of magnets of the fixed ring and a plurality of permanent magnets of the movable ring oppose the force caused by a person's weight. The repelling forces are transmitted to the femur and tibia and reduce the leg's load caused by the weight of a person.

The fixed ring could also rest on a belt with a stop located on the person's waist. In the absence of a load, the repelling forces displace the movable ring on a distance of 5 to 20 mm. The desired load sets the number of permanent magnets located on a fixed and movable ring. Some of the permanent magnets could be divided magnets.

BRIEF DESCRIPTION OF THE DRAWINGS

The present method and apparatus will be understood and appreciated from the following detailed description, taken in conjunction with the drawings and wherein like reference numerals denote like elements:

FIG. 14 is a second embodiment of a knee brace including a device maintaining a consistent force resistance force to a relative movement of the device elements;

FIG. 15 is a frontal view of the second embodiment of a knee brace of FIG. 14;

DETAILED DESCRIPTION OF ILLUSTRATIVE EMBODIMENTS

Definitions

Cartilage is a rubbery matter located between the thighbone or femur and shinbone or tibia. Cartilage acts as a cushion between the weight-bearing surfaces of the femur, and tibia reduces the friction between the bones.

Tibia is a massive leg bone located below the knee. The tibia connects the knee with the ankle bones.

The femur is the only bone in the upper leg and above the knee. It extends towards the knee, which forms a joint and connects through the knee, the femur with tibia.

A consistent-force device or spring is a spring for which the force it exerts over its range of motion does not vary much.

Interaction Between Permanent Magnets

Figure 1:
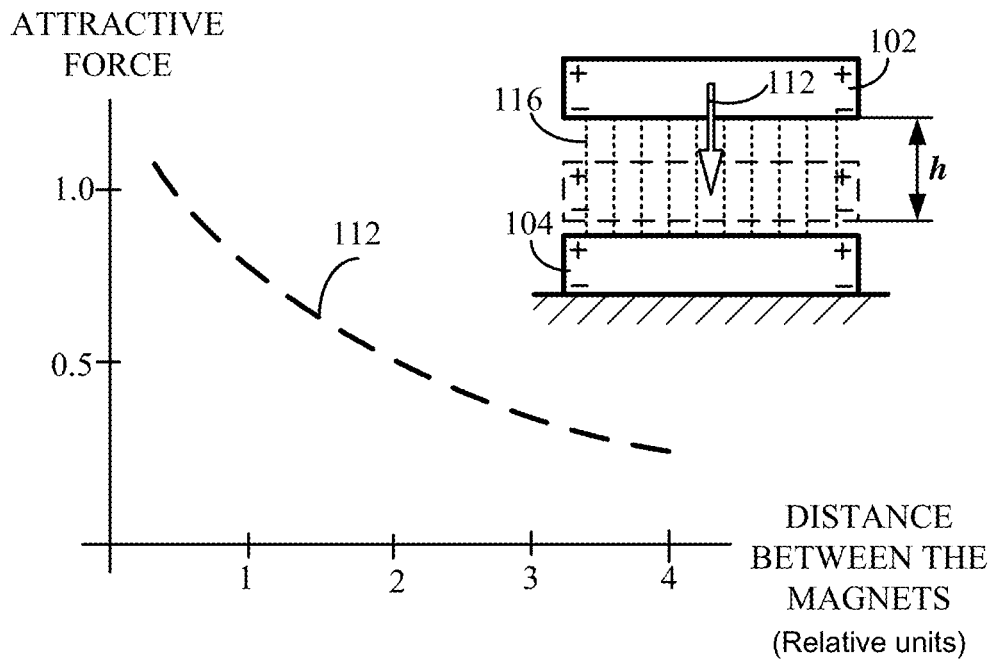
FIG. 1 is an example of prior art explaining the interaction between two permanent magnets with their poles oriented to attract the magnets to each other.
Figure 2:
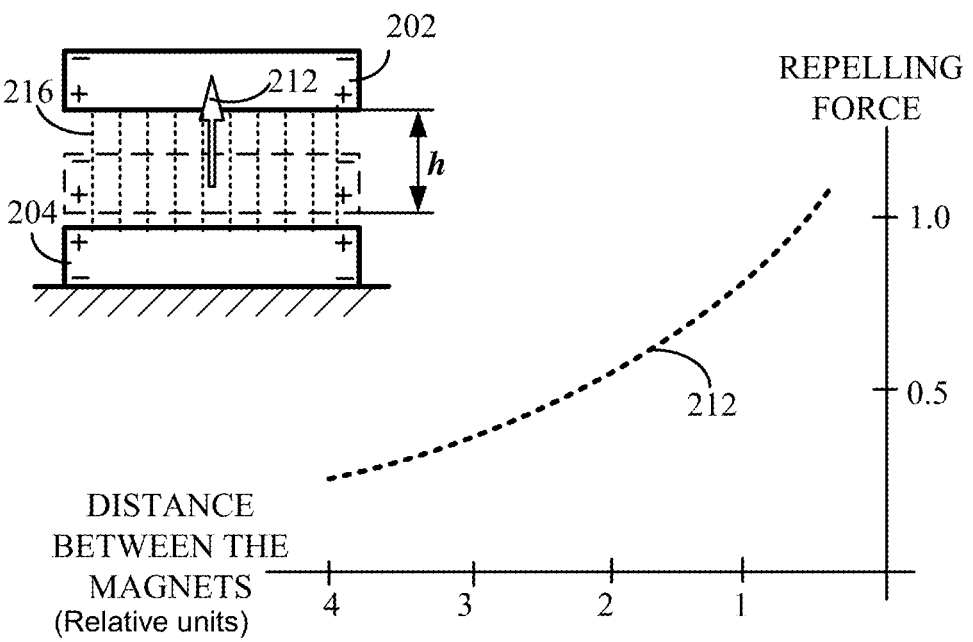
FIG. 2 is another example of prior art explaining the interaction between two permanent magnets with their poles oriented to repel the magnets from each other.

FIG. 1 illustrates the interaction between two permanent magnets 102 and 104 located vis-a-vis each other with their opposite poles oriented to attract the magnets to each other. The greater the distance h between permanent magnets 102 and 104, the weaker the force 112 of attraction between the magnets. Conventionally, lines between two magnets schematically show magnetic field forces 116 and 216 (FIG. 2). The magnetic field forces 116 and 216 are almost uniformly spread over the surface of the magnets. (The FIG. does not show some magnetic field forces fringing at the edges of permanent magnets.)

The repelling force 212 between two permanent magnets 202 and 204 located vis-a-vis each other with their identical poles (FIG. 2) is greater when the distance h between permanent magnets is shorter and weaker when the distance between two permanent magnets increases.

When the permanent magnets move relative to each other, the force of interaction between them could be used to resist or assist their movement or movement of an object to which the permanent magnets are attached. However, the force of interaction between two permanent magnets is effective only at a short distance, for example, three or five millimeters.

Walking Pattern Description

Figure 3:
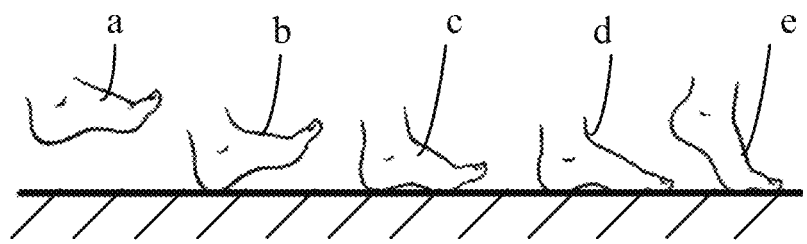
FIG. 3 is an example of a foot movement of a walking pattern of a person.

FIG. 3 is an example of a gait (walking pattern) of a person. The figure illustrates different positions of the foot of a walking person. In each step performed by the right and left legs of a walking person, support (leg rests on the floor or ground) and swing leg periods are distinguished. Typically, in the course of walking, one leg is in a support period/position, and the other leg is in a swing movement. The ratio of one leg's support position period to the swing period of another leg is typically 4:1. In FIG. 3, the leg is in a swing position (a), then the person steps on the heel of the foot (b), and the heel touches the floor first. The person gradually transfers the whole weight to the earlier flat foot phase (c). The early flat foot phase ends when the center of gravity of the person passes over the foot's top. This starts the period when the person stands on the entire foot (d). Next, the weight is shifted to the front part of the foot (e), the heel raises, and the foot pushes the weight away from the floor/support.

Figure 4:
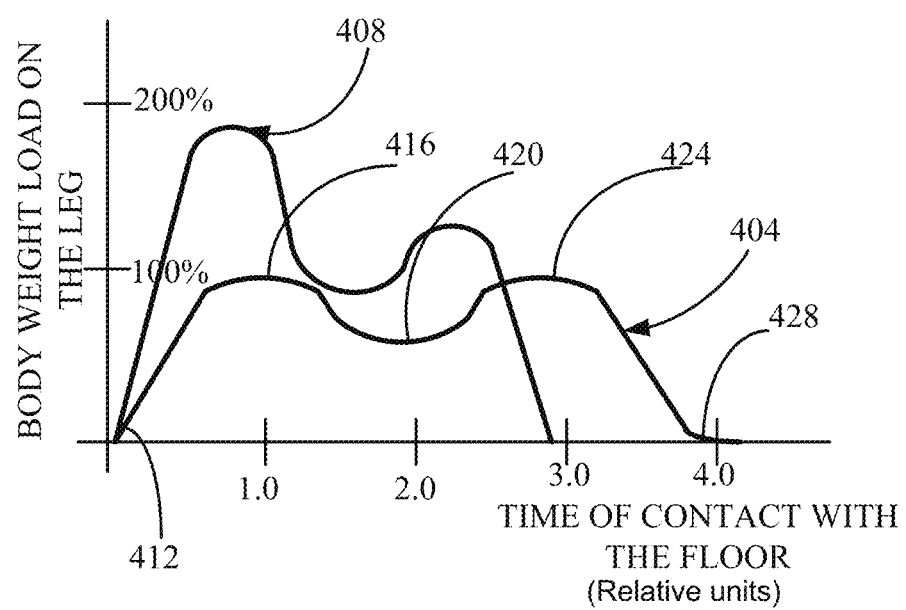
FIG. 4 is a graphical example of forces acting on a leg and knee in the course of walking.

FIG. 4 is a graphical example of forces acting on a leg and knee in the course of walking. The graph is a smooth two-humped curve 404. Both maxima 416 and 424 of graph 404, and at a slow walking, pace are almost equal to the body weight. At a brisk walking pace 408, the symmetry is lost, the maxima are about 120%-130%, and at a fast walking pace, the maxima are about 150% and 200% of the body weight. That is, the pressure acting on the leg and knee depends on the speed of movement: the faster a person moves, the higher are inertial forces and pressure on the floor (support) exerted by a leg.

In FIG. 4, numeral 412 marks the force acting on a leg when the foot touches the floor. As the foot continues to move, the force acting on a leg is growing. The force reaches a maximum at 416 when the weight of the person is on the heel of the foot, and the heel is on the floor. Numeral 420 marks a period when the entire foot is on the floor, and numeral 428 marks the moment when the foot is pushed away from the floor.

One of the knee problems is cartilage damage in the articulating joint connecting the tibia and femur. The cartilage may wear and tear slowly due to aging. It can also tear suddenly during sporting activities. Cartilage wear increases the friction between the weight-bearing surfaces of the femur and tibia and causes pain to a person. When the cartilage wears away, the cartilage protection between the joints is lost. The phenomenon is referred frequently to as "bone-on-bone" phenomenon. As the bones rub together, friction between the bones increases, and the joint continues to wear down the surface of the bones and could cause changes in the bone surface. The reduction of the force acting on the weight-bearing surfaces of the femur and tibia could alleviate the bone-on-bone problem.

Knee braces currently used to treat various knee problems do not support the alleviation of the bone-on-bone phenomenon. In the best case, the existing devices transfer weight from a damaged knee compartment to a healthy knee compartment of the same knee. The current solutions are also not useful for walking because they still cause undesired friction between some compartments of the knee.

The present device uses an arrangement of permanent magnets that generates a sufficient force and allows to reduce the forces acting between the leg bones (femur and tibia) and alleviates the bone-on-bone phenomenon. As the subject handles a load affecting the separation between the bones, the device generates a repelling force that reduces the force acting on the bones. The developed device includes at least three permanent magnets, although the use of only two magnets could bring similar results. Such a device, among others, could be used in a knee brace.

Figure 5:
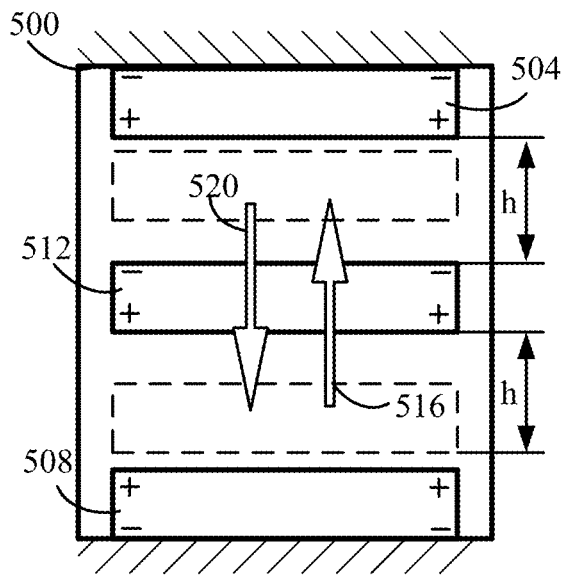
FIG. 5 is an example of a device including three permanent magnets.
Figure 6:
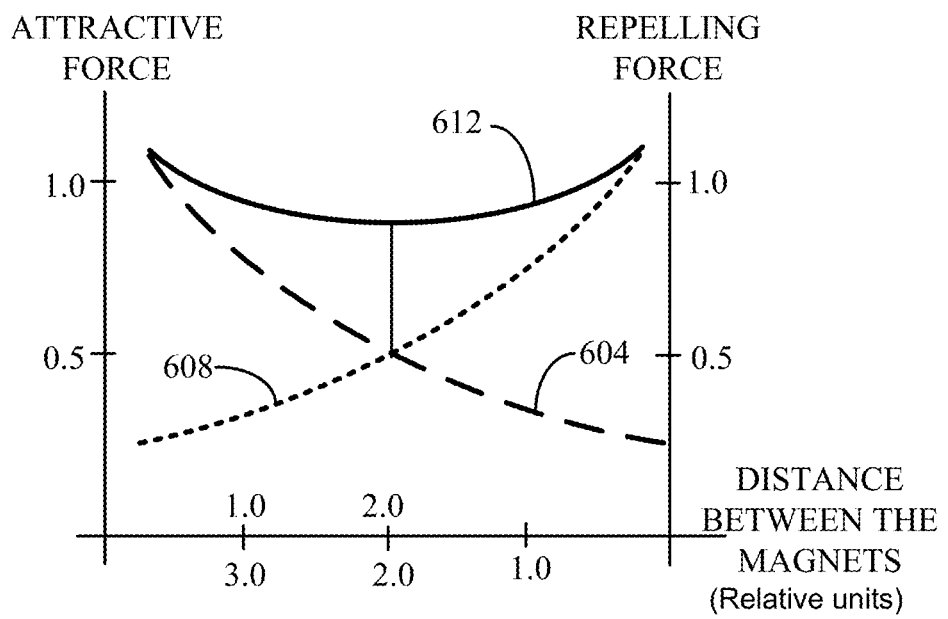
FIG. 6 is a graphical representation of the force resisting movement or displacement of one of the permanent magnets of FIG. 5.

FIG. 5 is an example of a device, including three permanent magnets. Two of the permanent magnets, 504 and 508, are located on a common substrate 500 and oriented, as illustrated. A third permanent magnet 512 is located between the first and second permanent magnets 504 and 508 and has a freedom of movement relative to permanent magnets 504 and 508. The third permanent magnet 512 has its poles oriented vis-à-vis identical poles of two magnets 504 and 508. As illustrated by arrows 516 and 520, movement or displacement of the third permanent magnet 512 towards each of permanent magnets 504 or 508 supports, as illustrated in FIG. 6, the maintenance of a consistent force resisting the movement of permanent magnet 512.

The magnetic field of permanent magnets 504, 508, and 512 defines the resistance to movement force. Curve 604 (FIG. 6) illustrates the change in the force of interaction between permanent magnets 512 and 504 when permanent magnet 512 moves (arrow 516) towards permanent magnet 504, and curve 608 illustrates the change in the force of interaction between permanent magnets 512 and 508 when permanent magnet 512 moves towards (arrow 520) permanent magnet 508. Curve 612 represents the force resisting the movement or displacement of permanent magnet 512. Curve 612 is a sum of curves 604 and 608 in each point along with the movement or displacement track of permanent magnet 512 and remains about consistent through the magnet 512 displacements. All listed above permanent magnets are selected such that the magnetic field of each of the permanent magnets is 0.2-10.0 Tesla.

Figure 7:
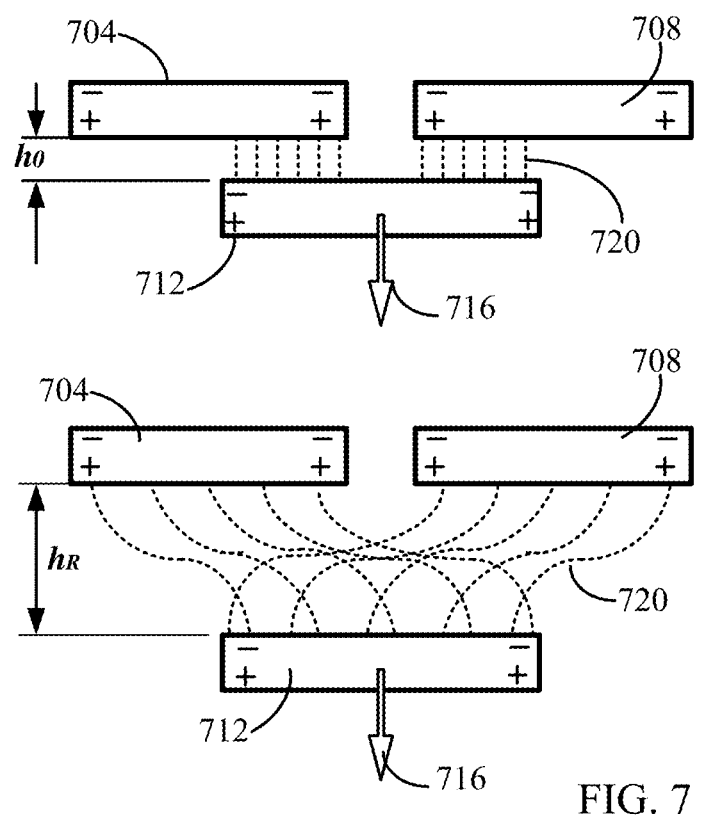
FIG. 7 is an example of further enhancement of the force resisting the movement or relative displacement of substrates with mounted on the substrates permanent magnets.

Further enhancement of the force resisting the movement or relative displacement of the permanent magnets could be achieved by splitting or dividing one of the permanent magnets into two parts, as illustrated in FIG. 7. Force 716 resisting the displacement of permanent magnet 712 is almost twice as large as the force developed by the configuration of FIG. 5. By convention, magnetic field lines trace the force between the magnets. The distance between the lines indicates the relative strength of the magnetic field. The closer the lines are, the stronger the magnetic field is. Reference numbers 704 and 708 mark a divided permanent magnet. Arrow 716 marks the direction of the displacement of permanent magnet 712. Magnetic field lines 720 mark the magnetic field interaction between permanent magnets 704, 708, and 712. FIG. 7 shows that the density of magnetic field lines 720 is the highest at the surface of permanent magnet 712. Thus, force 716 developed by the configuration is higher than the force developed by a single pair of permanent magnets.

In FIG. 7, the displaced or moving magnet 712 is located along the central axis between the stationary magnets 704 and 706. When the distance between moving magnet 712 and between the stationary magnets 704 and 706 is short, only the segments overlapping magnet 712 participate in the magnetic field interaction. The force of interaction between magnets is proportional to the size of interacting surfaces. The working surfaces of the permanent magnets that create these efforts are opposite to each other. The forces of attraction or repulsion acting on each of the stationary permanent magnets are equal to the value of the force acting on the permanent magnets of FIG. 5.

An increase in the force of interaction of the permanent magnets in the device could also be achieved by increasing the area of the magnets or by increasing the number of individual magnets used.

Figure 8:
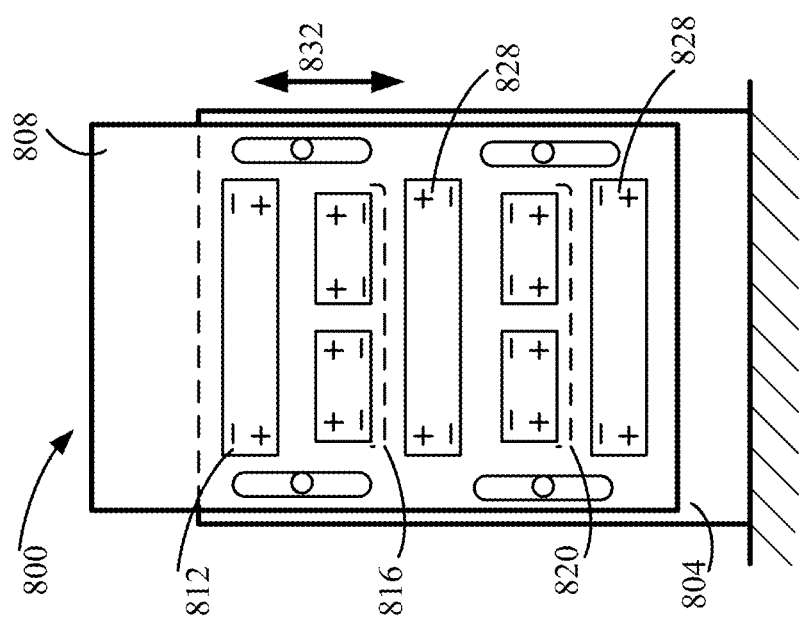
FIG. 8 is an example of a device maintaining a consistent force resisting to a relative movement between two substrates with permanent magnets.

FIG. 8 is an example of a device maintaining a consistent force resisting a relative movement between two substrates with permanent magnets. Device 800 maintains a consistent force resisting a relative movement between first substrate 804 and second substrate 808. Two permanent magnets, 816 and 820, located on a first substrate 804, are oriented, as illustrated in FIG. 8. To enhance the force resisting the displacement or movement of substrates 804 and 808 relative to each other, two permanent magnets, 816 and 820, are each divided into two parts.

Device 800 is an assembly of a first substrate 804 and a second substrate 808 located opposite each other. The clearance between the substrates exceeds the thickness of the permanent magnets on 0.2 to 0.3 mm. The assembly of device 800 supports the movement of substrate 804 relative to substrate 808. The assembly of device 800 also supports the placement of a pair of permanent magnets 816 and 820 of the first substrate 804 between the three permanent magnets 824, 828, and 812 of a second substrate 808. (Although, the substrates could include any other uneven or even number of magnets.) The assembly of the first substrate 804 with a pair of permanent magnets 816 and 820, and second substrate 808 with three permanent magnets 824, 828, and 812 support freedom of movement relative to each other, as shown in FIG. 8 by arrow 832. All permanent magnets are selected such that the magnetic field of each of the magnets is 0.2-10.0 Tesla.

Figure 9:
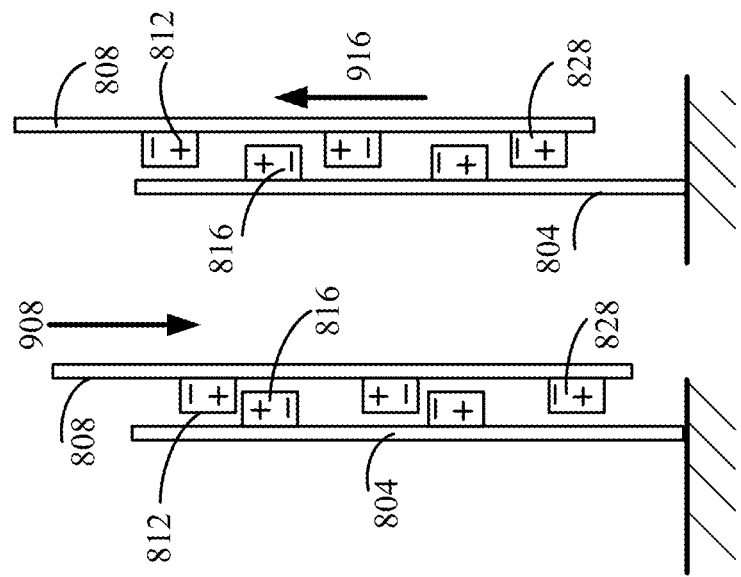
FIG. 9 is a side view illustrating the operation of device 800 in an unloaded and loaded state.

FIG. 9 is an example illustrating the operation of device 800 in an unloaded and loaded state. Load on device 800, schematically shown by arrow 908, moves substrate 808 in the direction of arrow 908. The force of interaction between permanent magnets 812, 816, 820, 824, and 828 resists this movement and maintains the separation between the permanent magnets. Upon removal of the load, substrate 808 returns, as shown by arrow 916 to the initial position.

Device 800 maintains a consistent force sufficient to support the adaption of the device for use in a knee brace, such that device 800 reduces the forces acting between the femur and tibia and alleviates the bone-on-bone phenomenon.

Figures 10, 11:
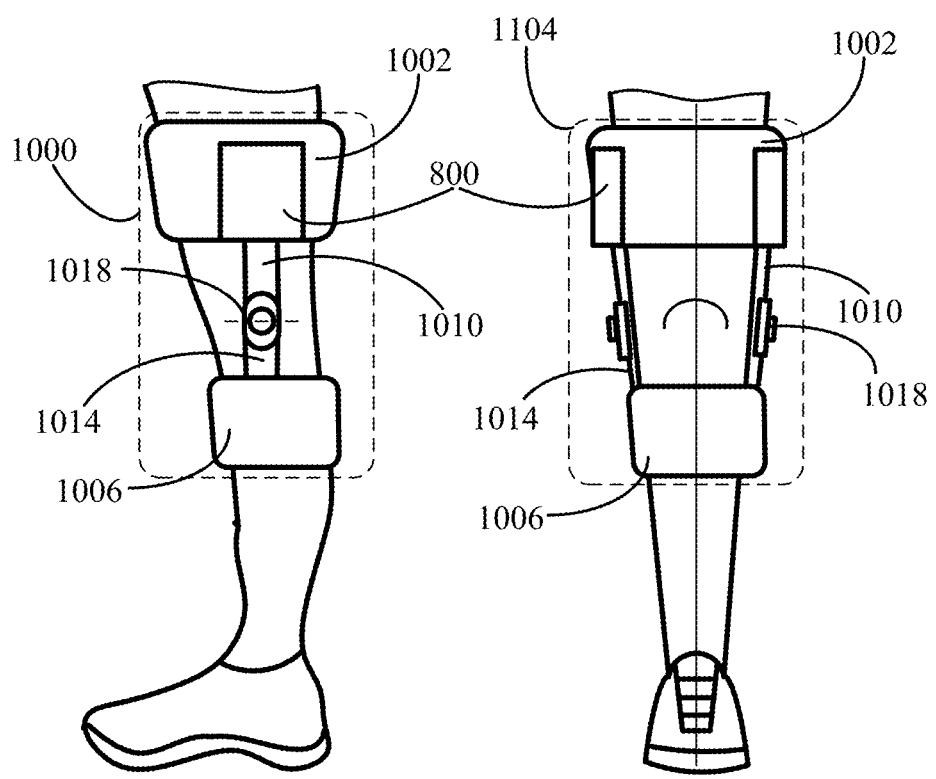
FIG. 10 is a first embodiment of a knee brace, including a device maintaining a consistent resistance force between the femur and tibia.
FIG. 11 is a frontal view of the first embodiment of a knee brace of FIG. 10.

FIG. 10 is an example of a knee brace, including a device maintaining a consistent resistance force between the femur and tibia. Device 800 maintains a consistent resistance force to a relative movement of the device substrates. Knee brace 1000 includes a femur cuff 1002 and a tibia cuff 1006. A device 800 (FIG. 8) could be embedded in femur cuff 1002 or attached to the outer surface of femur cuff 1002. Device 800 is operatively connected with tibia cuff 1006 with the help of femur lever 1010 and tibia lever 1014. A hinge 1018 connects between device 800 and femur lever 1010 and tibia lever 1014. Hinge 1018 supports displacement of the tibia with the help of cuff 1006 attached to the tibia relative to device 800 and femur cuff 1002. Hinge 1018 also supports rotation or flexion of the tibia cuff and the tibia relative to the femur.

FIG. 11 is an elevation view of an example of a knee brace of FIG. 10. Knee brace 1000 includes one device 800 and a system of levers 1010 and 1014. Knee brace 1104 of FIG. 11 includes a pair of devices 800 and a pair of lever systems 1010 and 1014. Knee brace 1104 configuration supports greater weight and pressure handled by cuffs 1002 and 1006 and levers 1010, 1014 than knee brace 1000 supports. Magnets of device 800 reduce the force acting on the foot in the course of walking, and also reduce the force when there is no pressure on the foot.

Permanent magnets inserted into the knee joints (US20050251080 to Hyde, U.S. Pat. No. 8,029,570 to Barnes, and U.S. Pat. No. 5,879,386 to Jore) reduce the load on the knee when a person is wearing them, for example, stands on the floor or other support surface. Magnets inserted into the knee joints create a negative load (FIG. 12) on the leg if the leg is not loaded. Therefore, such magnetic devices cannot create a significant relief on the knee. An increase in the number of permanent magnets inserted in the joint helps to support larger weights; however, the knee joint's negative load also increases. Additionally, there is little space in the knee.

Figure 12:
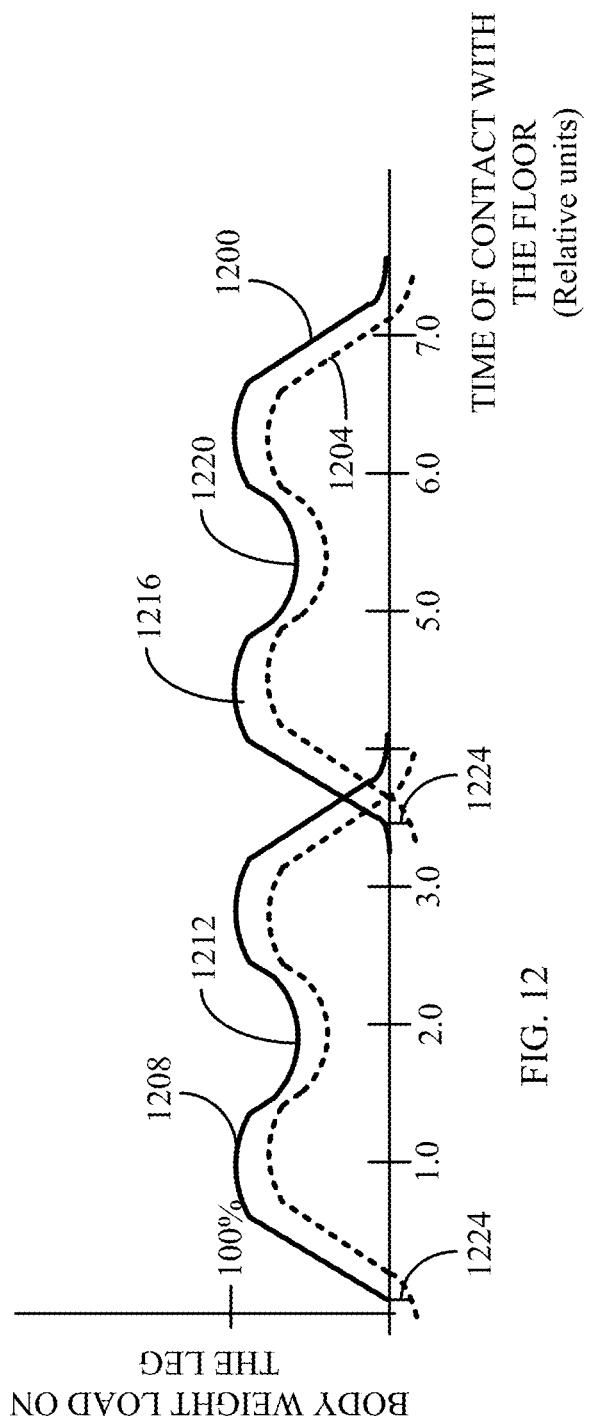
FIG. 12 is a schematic illustration of a load on the knee with permanent magnets inserted in the knee.

FIG. 12 is a schematic illustration of a load on the knee with surgically inserted in the knee permanent magnets. Line 1200 marks a regular load on the knee without the use of magnets. Brocken line 1204 marks the load on a knee with permanent magnets inserted in the knee. Reference numeral 1208 marks, for example, a period when the heel of the left leg is on the floor and acts to support the weight. Reference numeral 1212 marks the period when the whole foot is on the floor. Numeral 1214 marks the left leg swing period. Numerals 1216 and 1220 mark corresponding periods of the right leg. Dimension 1224 between the broken line and X-axis of the figure illustrates the negative load on the knee.

When a person wearing a brace including a device 800 (FIG. 8) steps on the leg, the load on brace/device 800 grows (FIG. 14), and device 800 takes upon it a certain load/weight. Despite the load, device 800 maintains the resistance force, reducing friction between the bones and removing the pain associated with the bone-on-bone phenomenon. When a person flexes a leg, device 800 maintains a constant load between the tibia and femur. Not like spring based devices, device 800 does not accelerate the flex movement of the tibia. Further to this, device 800 is a device thinner (seven to nine-millimeter thick) than the existing mechanical devices. The device is flat and could be worn under the closes and as close as possible to the leg.

Figure 13:
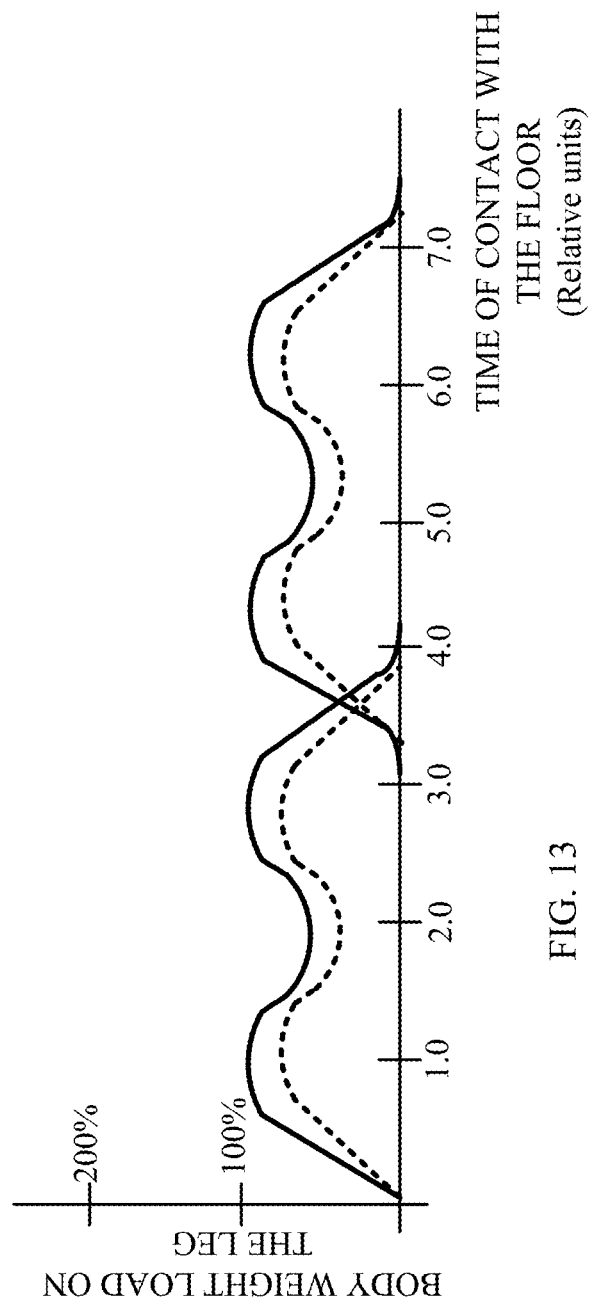
FIG. 13 is a schematic illustration of a load on the knee of a person that wears the present knee brace.

FIG. 13 is a schematic illustration of a load on the knee of a person that wears the current knee brace. The disclosed device does not generate a negative load on the knee.

Knee brace with a single device 800 (FIG. 10) using permanent magnets with a magnetic field of about 0.8-0.9 Tesla develops a resistance force of almost 6 kg. Knee brace 830 (FIG. 11) includes two devices 800 and a repelling force of about 12 kg per knee. Permanent magnets with a larger magnetic field could provide a larger repelling force.

When a person wearing brace 1000 or 1104 sits or makes a swing in the air while walking, then the knee does not experience any load caused by the weight of the person. The force acting on the legs is minimal. When the person touches the ground, a load on the knee joint caused by the weight of the person appears. The load moves plate 808, as shown by arrow 908, the permanent magnets come closer to each other, and the force is opposing the load caused by the weight of the person increases.

When in the course of walking, a leg of a person comes off the floor (support), or the person is sitting, then the substrate 808 returns to unloaded (arrow 916) position (FIG. 9). The distance between the magnets increases, and the pressure on the knee joint decreases.

FIG. 14 is another example of a knee brace, including a device maintaining consistent resistance force to a relative movement of the device elements. Lever 1404 of a knee brace 1400 extends the length of the leg and, in one example, enters shoe 1408. Lever 1404 rests against sole 1412. In another example, lever 1404 could be inserted into a lever 1404, receiving nest 1504 (Detail D) attached to shoe 1408. Receiving nest 1504 could be arranged to allow lever 1404 to pass through and reach a stable basis, such as the floor. To maintain the linear movement of lever 1404, additional guides 1416 could be attached to cuff 1410. If desired, cuff 1410 could be extended to cover a large segment of the leg.

The advantage of knee brace 1400 (the example of FIG. 14 and FIG. 15) is that lever 1404 is resting on a stable basis.

Device 800 acts to move femur cuff 1402 with the femur to which cuff 1400 is attached. Despite the load, device 800 maintains a consistent resistance force between the tibia and femur, preventing friction between the bones and removing the pain associated with the bone-on-bone friction. When a person flexes a leg, device 800 maintained a constant load and maintained the separation between the tibia and femur. Not like spring devices, device 800 does not accelerate the flex movement of the tibia.

Figure 16:
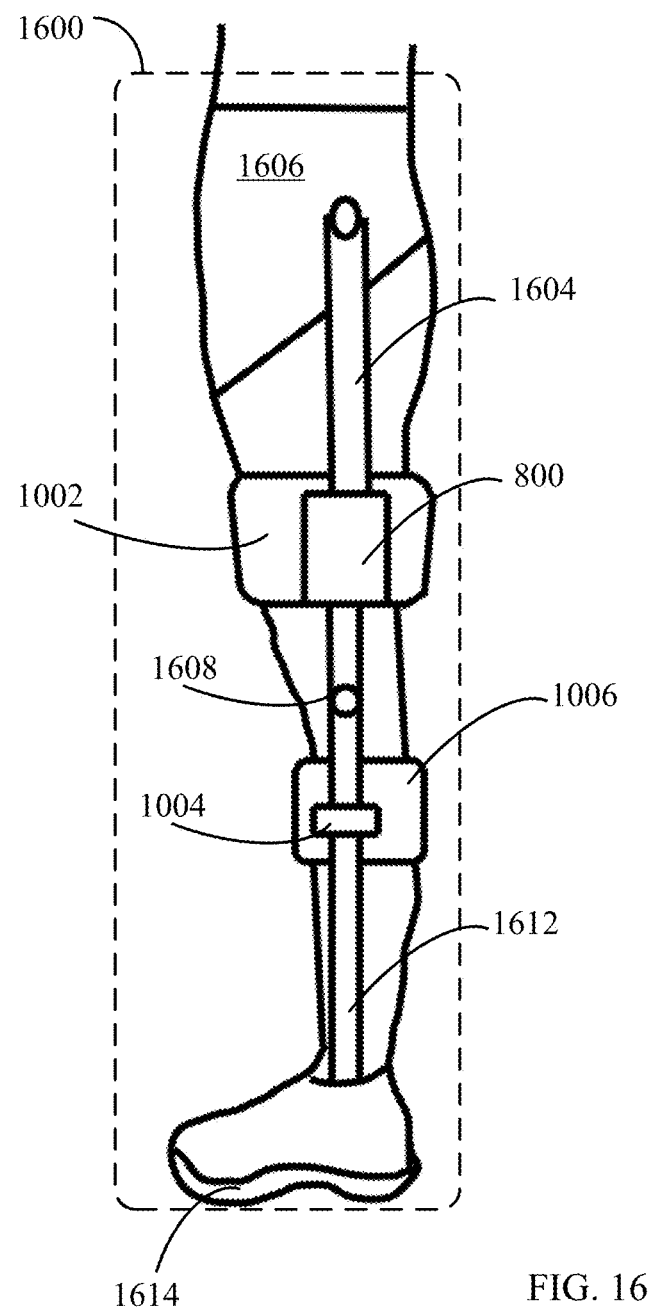
FIG. 16 is a third embodiment of a knee brace including an assembly of permanent magnets.

FIG. 16 is an additional example of a knee brace, including a device maintaining a consistent resistance force to a relative movement of the device elements. Knee brace 1600 includes a lever 1604 extending along the leg and connecting to hinge 1608. The other end of lever 1604 terminates on a corset 1606 that could be a rigid or partially rigid corset. Femur cuff 1002, together with corset 1606, provides sufficiently rigid support that could limit lever 1504 movement. Femur cuff 1602 includes device 800. Lever 1612 extends from hinge 1608 and could rest against sole 1614. In another example, lever 1608 could be inserted into a lever 1608, receiving nest (not shown) similar to receiving nest 1406 (FIG. 14). Receiving nest 1406 could be arranged to allow lever 1612 to pass through and reach a stable basis, such as the floor.

Figure 17:
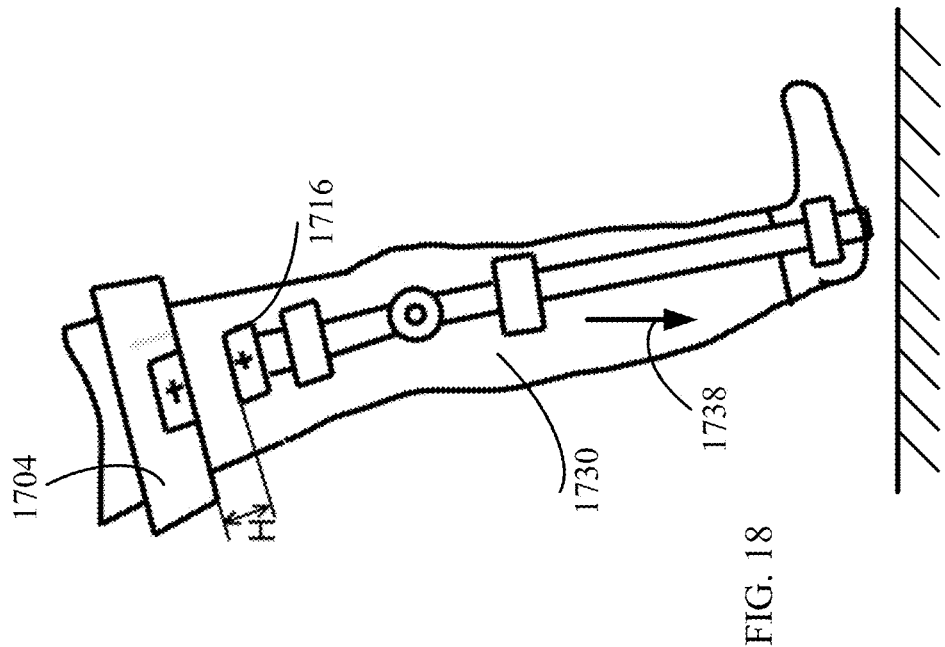
FIG. 17 is an example of a device for reducing the load between the weight-bearing surfaces of a knee.

FIG. 17 is an example of a device for maintaining a consistent resistance between the weight-bearing surfaces of the knee. Device 1700 includes two arrays of permanent magnets; one array of permanent magnets 1704 located and fixed on a ring 1708. The user of the device wears ring 1708 on his or her thigh. Another array of permanent magnets 1716 could be located on movable plate/ring (not shown) 1716 located opposite ring 1708 carries another array of permanent magnets 1720. Some permanent magnets of the arrays 1704 and 1716 could be divided magnets. Lever 1724 connects movable plate 1716 to a hinge mechanism 1728. When a person steps on a leg 1730, the load (arrow 1734) reduces the clearance or separation between the magnets to a value h. The repelling forces between the permanent magnets increase and counteract the force acting between the femur and tibia and the related to the bone-on-bone phenomenon pain. A desired repulsive force sets the number of permanent magnets located on the fixed and movable rings.

Figure 18:
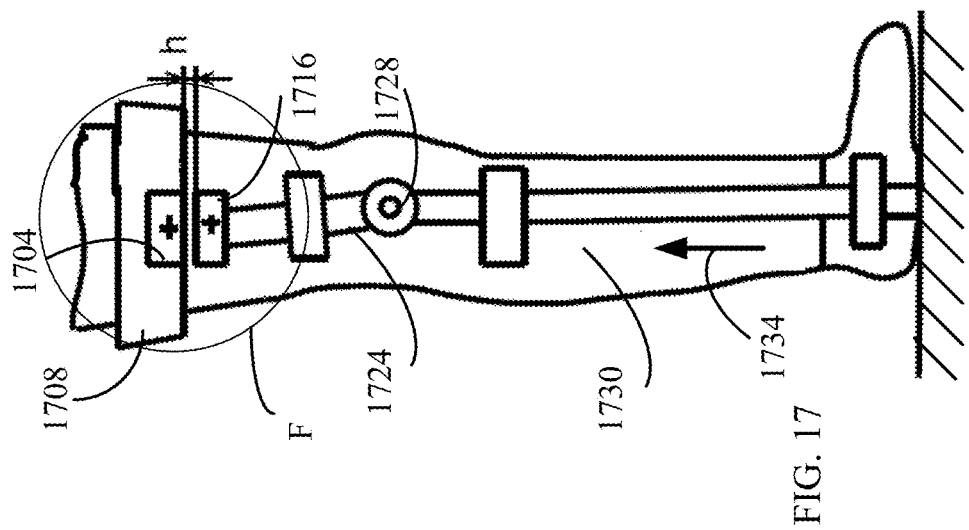
FIG. 18 illustrates a leg with a device of FIG. 17 in a swing movement.

FIG. 18 illustrates a leg with a device of FIG. 17 in a swing movement. When a person's leg is in the air, for example, in a swing movement or while walking, the load from the weight of the person to the knee joint becomes zero. The distance between the arrays of permanent magnets 1704 and 1716 increases. The force of interaction between the permanent magnets decreases. The opposing load force does not exist.

The interaction between permanent magnets 1704 and 1716 pushes leg 1730 away (Arrow 1738), and the knee joint does not experience any strain between the femur and tibia. The interaction between the permanent magnets removes any possible pain. In the absence of a load, the repelling forces of device 800 displace the movable ring 5 to 20 mm.

Figure 19:
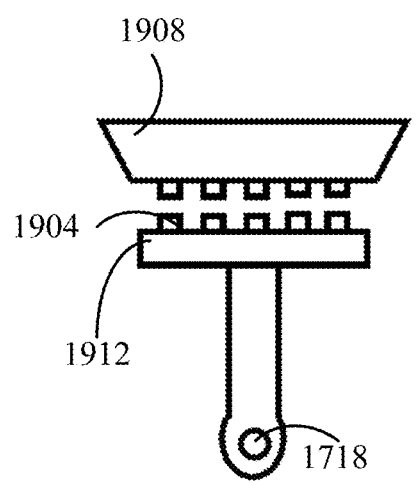
FIGS. 19 through 21 illustrate some examples of permanent magnets assemblies built-into the rings of knee brace of FIGS. 17-18.
Figure 20:
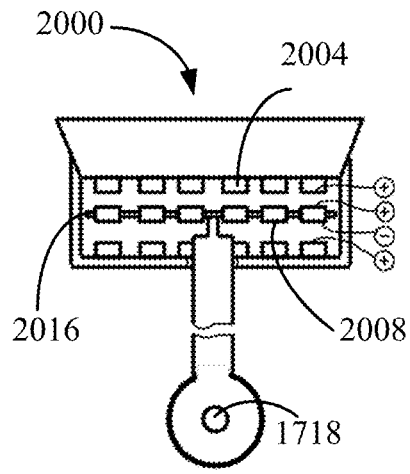
Figure 21:
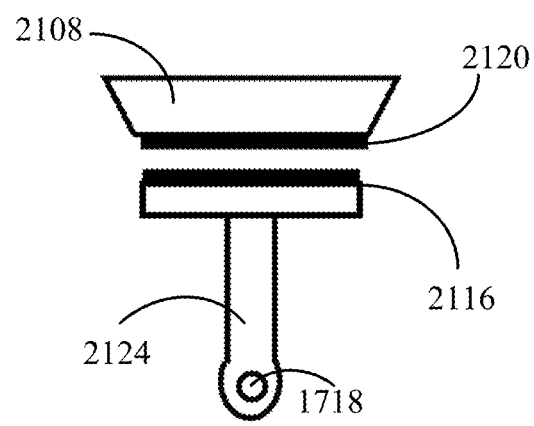
Figure 22:
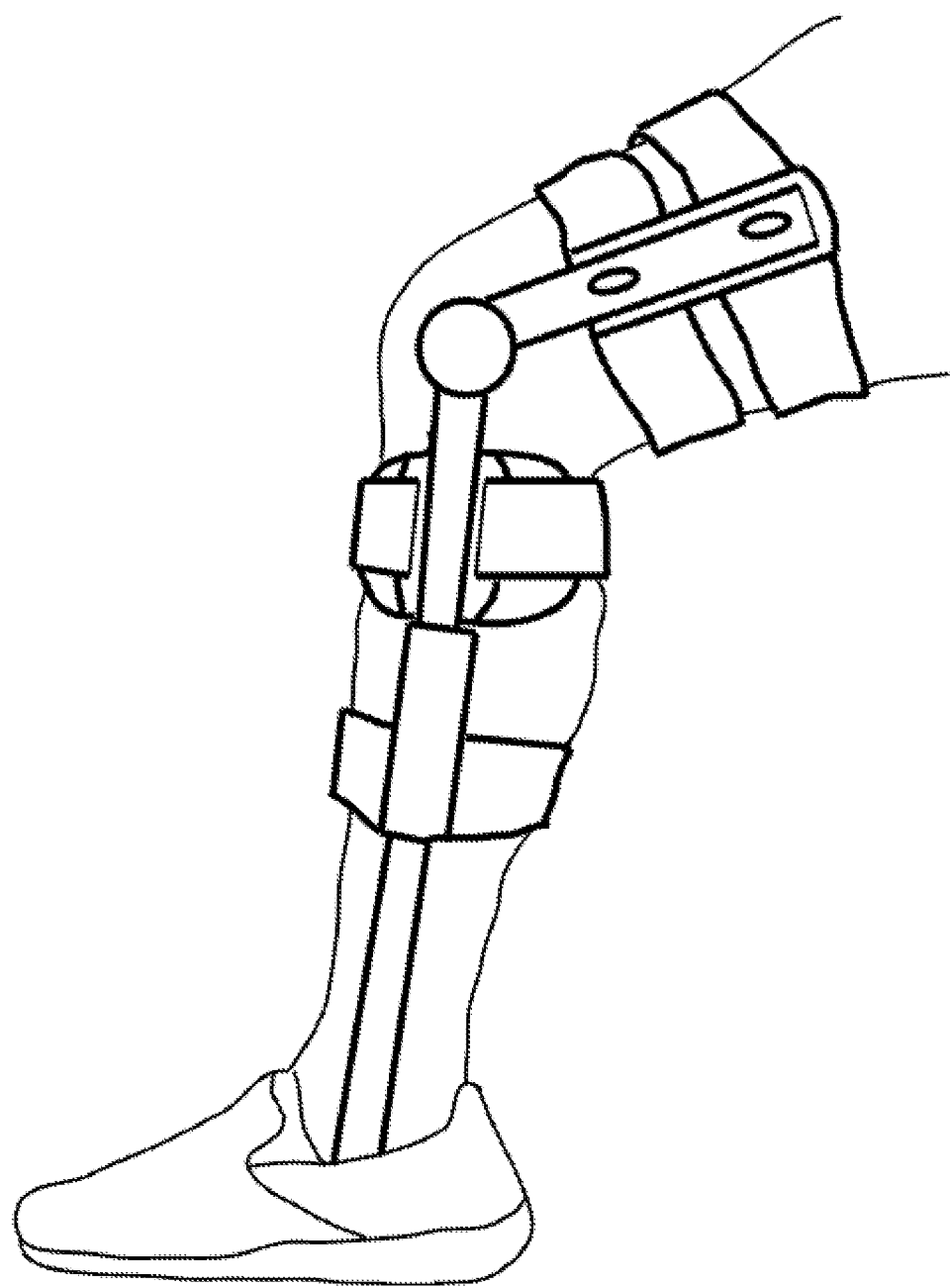
FIG. 22 is a photograph of an interior side of a leg with a knee brace embodied in accordance with the present disclosure.
Figure 23:
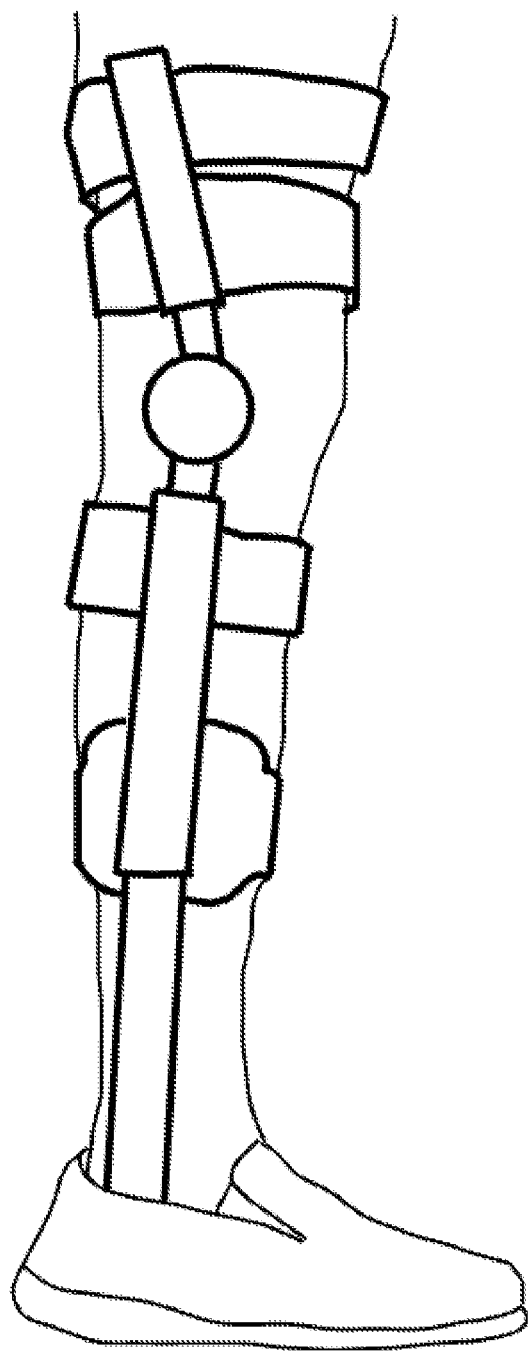
FIG. 23 is a photograph of an exterior side of the leg with a knee brace of FIG. 22.
Figure 24:
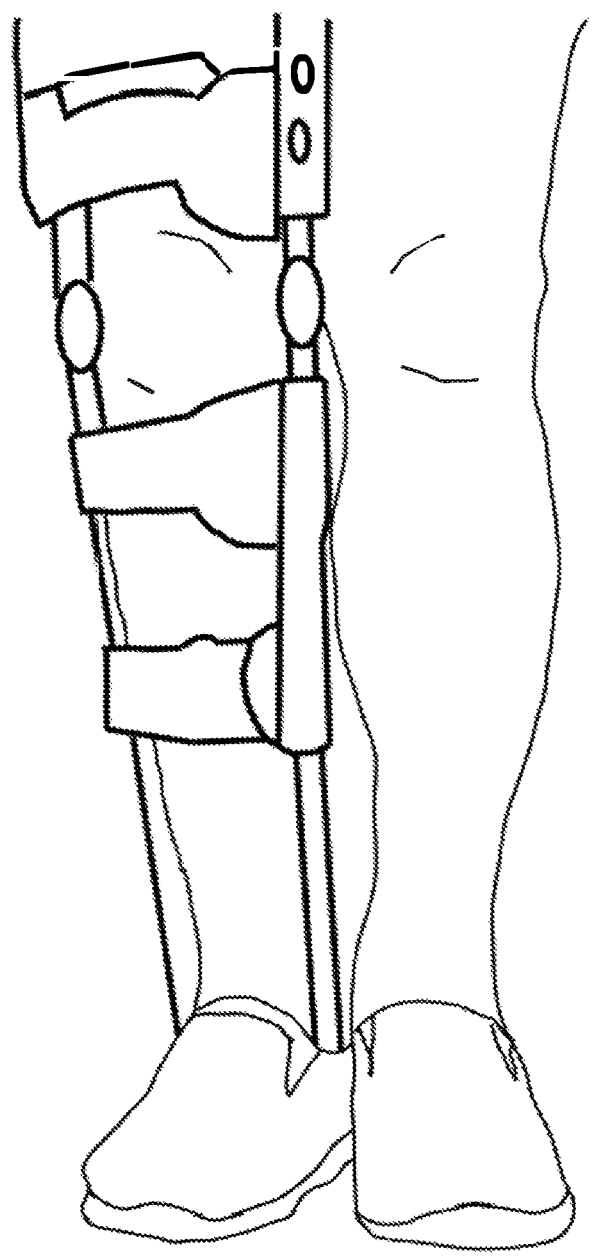
FIG. 24 is a photograph of a front side of the leg with a knee brace of FIG. 22.

FIGS. 19 through 21 illustrate some examples of permanent magnets assemblies built into the rings of knee brace of FIGS. 19-18.

FIG. 19 illustrates an assembly of permanent magnets 1904 built-in into ring 1908 and 1912. FIG. 20 illustrates an assembly of arrays of permanent magnets 2004, in addition to described earlier permanent magnets built-in into rings 1908 and 1912. Device 2000 includes an assembly of permanent magnets 2008 assembled on an additional (third) movable/displaceable ring 2016 connected to a hinge 1718. The arrangement of magnets in FIG. 20 increases the uniformity and strength of the magnetic field, acting on the rings and leg.

FIG. 21 illustrates a magnetic device using two magnetic material strips 2120 and 2116. The strips are attached to corresponding rings connected to a lever 2124.

Described is a knee brace. The brace is small and thin, which allows the person to wear it underneath trousers or other clothing items. It is made of lightweight materials and does not put extra weight on the leg of a person.

Device 800 maintains a consistent force throughout the dynamic range of knee joint extension and flexion, particularly as experienced during the swing phase of gait.

The use of device 800 was described in the environment of a knee brace. It will be appreciated that the magnetic spring 800 of the device can advantageously be used in many other applications, and the principles of the device 800 will apply equally. One of such applications could be posture correction braces.

It is to be understood that the description of the foregoing exemplary embodiment(s) is (are) intended to be only illustrative, rather than exhaustive. Those of ordinary skill will be able to make certain additions, deletions, and/or modifications to the embodiment(s) of the disclosed subject matter without departing from the spirit of the disclosure or its scope.

What is claimed is:

1. A device for reducing a load on a knee joint of a person in the course of walking, comprising:
    a fixed ring to be worn on a thigh of the person, the fixed ring populated by a plurality of first permanent magnets;
    a movable ring populated by a plurality of second permanent magnets oriented to repel the first permanent magnets located on the fixed ring;
    at least one rigid lever, one end of which is attached to the movable ring and the other end of which is for location at a knee level of the person, the at least one rigid lever containing a hinge;
    at least one additional rigid lever, a proximal end of which is connected to the hinge and a distal end of which abuts against a guide and is for resting on a floor; and
    wherein the at least one additional rigid lever is configured to push the movable ring populated by the second permanent magnets towards the fixed ring when the person walks; and
    wherein repelling forces acting between the first permanent magnets of the first ring and the second permanent magnets of the movable ring counteract the load on the knee joint in the course of walking.

2. The device of claim 1, wherein the fixed ring rests on a belt with a stop located on the waist of the person.

3. The device of claim 1, wherein the repelling forces displace the movable ring 5 to 20 mm in the absence of a load.

4. The device of claim 1, wherein the number of the first permanent magnets and the number of the second permanent magnets produces a desired repulsive force.

5. The device of claim 1, wherein at least one of the first and second permanent magnets is a divided magnet.

6. The device of claim 1, wherein the first permanent magnets are formed of a first flexible magnet band and the second permanent magnets are formed of a second flexible magnet band.

7. A method for reducing a load on a knee joint of a person in the course of walking, comprising:
    attaching a fixed ring to a thigh of the person, the fixed ring populated by a plurality of first permanent magnets;
    attaching a movable ring to the thigh of the person so as to be spaced from the fixed ring, the movable ring being populated by a plurality of second permanent magnets oriented to repel the first permanent magnets located on the fixed ring;
    attaching an end of at least one rigid lever to the movable ring, the at least one rigid lever having a hinge;
    locating the other end of the least one rigid lever at a knee level of the person;
    connecting a proximal end of at least one additional rigid lever to the hinge;
    connecting a distal end of the at least one additional rigid lever against a guide and resting the distal end on a floor; and
    wherein the at least one additional rigid lever is configured to push the movable ring populated by the second permanent magnets towards the fixed ring when the person walks; and
    wherein repelling forces acting between the first permanent magnets of the first ring and the second permanent magnets of the movable ring counteract the load on the knee joint in the course of walking.

8. The method of claim 7, wherein the fixed ring rests on a belt with a stop located on the waist of the person.

9. The method of claim 7, wherein the repelling forces displace the movable ring 5 to 20 mm in the absence of a load.

10. The method of claim 7, wherein the number of the first permanent magnets and the number of the second permanent magnets produces a desired repulsive force.

11. The method of claim 7, wherein at least one of the first and second permanent magnets is a divided magnet.

12. The method of claim 7, wherein the first permanent magnets are formed of a first flexible magnet band and the second permanent magnets are formed of a second flexible magnet band.

* * * * *